United States Patent
Elstrom et al.

(10) Patent No.: US 6,887,239 B2
(45) Date of Patent: May 3, 2005

(54) PREPARATION FOR TRANSMISSION AND RECEPTION OF ELECTRICAL SIGNALS

(75) Inventors: Tuan A. Elstrom, Lake Bluff, IL (US); Scott Kellogg, Boston, MA (US); Joseph Kost, Cambridge, MA (US); Samir S. Mitragotri, Arlington, MA (US); Nicolas F. Warner, Belmont, MA (US); Steve DiMatteo, Warren, RI (US)

(73) Assignee: Sontra Medical Inc., Cambridge, MA (US)

( * ) Notice: Subject to any disclaimer, the term of this patent is extended or adjusted under 35 U.S.C. 154(b) by 0 days.

(21) Appl. No.: 10/411,156

(22) Filed: Apr. 11, 2003

(65) Prior Publication Data

US 2004/0039418 A1 Feb. 26, 2004

Related U.S. Application Data

(60) Provisional application No. 60/372,814, filed on Apr. 17, 2002.

(51) Int. Cl.[7] .............................................. A61B 18/18
(52) U.S. Cl. ............................................ 606/41; 601/2
(58) Field of Search .......................... 601/2, 3; 606/32, 606/41, 47, 49; 607/115–116; 600/373–386, 508–528

(56) References Cited

U.S. PATENT DOCUMENTS

| | | | |
|---|---|---|---|
| 5,947,921 A | 9/1999 | Johnson et al. | |
| 6,113,561 A | 9/2000 | Augustine | |
| 6,126,619 A | 10/2000 | Peterson et al. | |
| 6,234,990 B1 | 5/2001 | Rowe et al. | |
| 6,321,109 B2 | 11/2001 | Ben-Haim et al. | |
| 6,463,314 B1 | 10/2002 | Haruna | |

*Primary Examiner*—Roy D. Gibson
*Assistant Examiner*—Aaron Roane
(74) *Attorney, Agent, or Firm*—Hunton & Williams LLP

(57) ABSTRACT

The invention provides a convenient and non-invasive means to prepare cells, tissues, and organs for electrical transmission and reception. In an embodiment of the invention, a control method comprises the use of at least one skin electrode, as a reference electrode, and an electrical sensor to measure periodically or continuously the skin's electrical conductance at the site of preparation. The dynamic change in the conductance through the skin is measured while the ultrasound is applied. Signal processing is performed on the measurement and the level of skin impedance change is controlled by performing a mathematical analysis and using the results of such analysis to control the application of ultrasonic energy. A desired level of skin impedance can be set at a predetermined value or based on a chosen level of skin integrity, subject's sensation of discomfort, or duration of the ultrasound application.

22 Claims, 14 Drawing Sheets

PREPARATION FOR TRANSMISSION AND RECEPTION OF ELECTRICAL SIGNALS

CROSS-REFERENCE TO RELATED APPLICATION

The present application claims priority to U.S. Provisional Patent Application No. 60/372,814 filed on Apr. 17, 2002, entitled "Preparation For Transmission and Reception of Electrical Signals," which is hereby incorporated by reference in its entirety, and is related to U.S. patent application Ser. No. 09/868,442 filed on Dec. 17, 1999, entitled "Method And Apparatus For Enhancement Of Transdermal Transport," which is also hereby incorporated by reference in its entirety.

BACKGROUND OF THE INVENTION

1. Field of Invention

The present invention relates to systems and methods of conditioning biological cells, tissues, and organs to facilitate enhanced electrical and bioelectrical transmission and reception of electrical potentials and currents.

2. Description of Related Art

Electrical signals provide useful tools to investigate and affect properties and functioning of biological materials. Electrical signals can be transmitted into biological entities such as cells, tissues, and organs to interrogate or stimulate the electrical properties of these biological entities. Electrical signals can also be naturally produced by biological cells, tissues, and organs in performing their functions within living animals and humans. The emission of bioelectrical signals from cells, tissues, and organs provide useful information about the condition and functioning of these entities. This information is important in the diagnosis of medical illness and conditions. The transmission of electrical signals into cells, tissues, and organs can have therapeutically beneficial effects for various medical ailment and diseases.

Bioelectrical signals such as bioelectrical potentials and bioelectric currents are monitored and recorded using electrodes attached to skin. These signals may be used to diagnose and treat various medical illness and conditions. For example, an electrocardiogram (ECG or EKG) records bioelectrical activities of the heart. Electroencephalograms (EEG) and evoked-response potentials (ERP) record bioelectrical activities of the brain. An electromyogram (EMG) records the electrical activities of a muscle. In addition, electrical signals can be applied and subsequently monitored to assess the functioning of other organs, for example, stimulation of nerves and measuring the conduction of the stimulus.

Electrical signals may be applied to a patient to treat biological organs; to deliver medication into cells, tissues, and/or organs, and to destroy various natural and foreign biological materials in animals and humans. In addition, electrical signals from human organs may be used for medical diagnosis, as described above, and also may be used to improve the actuation of external machinery such as bionic prostheses and computer-controlled vehicles such as automobiles and airplanes.

The transmission and reception of electrical signals through human skin is hindered by the presence of the skin's outer-most barrier, called the stratum corneum. For example, signal fidelity of bioelectrical potentials and currents measured through skin is degraded by the high impedance of the stratum corneum. Accordingly, the high impedance presents a problem to the ideal transmission and the measurement of bioelectrical signals from human cells, organs, and tissues.

It is well known that the removal of the stratum corneum reduces the high impedance of the skin and allows better transmission and reception of electrical signals into and from human organs. Invasive methods and devices have been devised to better prepare the location of skin where electrodes are placed for making electrical measurements. For example, typical invasive methods require the abrasion of skin with sand paper and brushes, the stripping of skin with tape and toxic chemicals, the removal of stratum corneum by laser or thermal ablation, or the puncturing of skin with needles. The preparation of skin by these methods may be laborious, time consuming, highly variable, hazardous, painful to the subject, and generally inconvenient.

SUMMARY OF THE INVENTION

The present invention seeks to overcome or reduce one or more of these or other deficiencies of the related art by providing a convenient, rapid, non-invasive system and method of skin preparation for the transmission and reception of electrical signals through animal or human cells, organs, and tissues such as skin.

It is an object of the present invention to control the application of ultrasonic energy applied to the coupling media and the ultrasound's subsequent effect on the properties of skin as to reduce the skin's electrical impedance.

In an embodiment of the invention, a control method comprises the use of at least one skin electrode or handgrip applicator electrode, as a reference electrode, and an electrical sensor to measure periodically or continuously the skin's electrical conductance at the site of preparation. The dynamic change in the conductance through the skin is measured while the ultrasound is applied. Signal processing is performed on the measurement and the level of skin impedance change is controlled by performing a mathematical analysis and using the results of such analysis to control the application of ultrasonic energy. A desired level of skin impedance can be set at a predetermined value or based on a chosen level of skin integrity, subject's sensation of discomfort, or duration of the ultrasound application.

It is another objective of the present invention to control the application of other forms of energy such as coherent and non-coherent electromagnetic energy, thermal energy, and magnetic energy to reduce the electrical impedance of cells, tissues, and organs.

In an embodiment of the invention, a control method comprises the use of at least one skin electrode, as a reference electrode, and a sensor to measure periodically or continuously the impedance change at a specific or general location of cells, tissues, and organs. The change in the impedance of cells, tissues, and organs is monitored while electromagnetic energy, thermal energy, and/or magnetic energy is applied. Signal processing is performed on the measurement and the level of skin impedance change is controlled by performing a mathematical analysis and using the results of such analysis to control the application of the mentioned energy sources.

It is a further object of the invention to provide a lead compatible with an ultrasonically prepared skin site.

In an embodiment of the invention, a lead is calibrated using the skin impedance value determined during skin preparation via the ultrasonic skin preparation system. The lead enables compensation for differences in the impedance of prepared skin sites due to site-to-site skin parameter variability. Although a skin site has been prepared to achieve pre-determined impedance, the final level of impedance at the particular site may be dependent upon other variables such as the level of discomfort for the subject. The lead can be programmed with a specific impedance for optimal transmission of signals to the input of diagnostic machines such as EEGs, EKGs, EMGs, ECGs, ERPs, electrosomnographic monitors, and Holter meters. Moreover, the lead can comprise a disposable screen-printed biosensors having a layer of hydrogel for making electrical contact with skin.

It is a further object of the invention to provide a system for ultrasonically preparing a plurality of skin sites for improved bioelectrical signal measurement.

In an embodiment of the invention, an array of ultrasonic applicators can be incorporated into a garment in the form of a flat sheet for application on the chest or in the form of a headgear for skin preparation. These arrays can aid in the mapping of the chest and brain during tomographic 2-dimension and 3-dimensional analysis of bioelectrical signals. Ultimately, the arrays can enhance the performance and fidelity of impedance spectroscopy and impedance imaging.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE PREFERRED EMBODIMENTS

Figure 1:
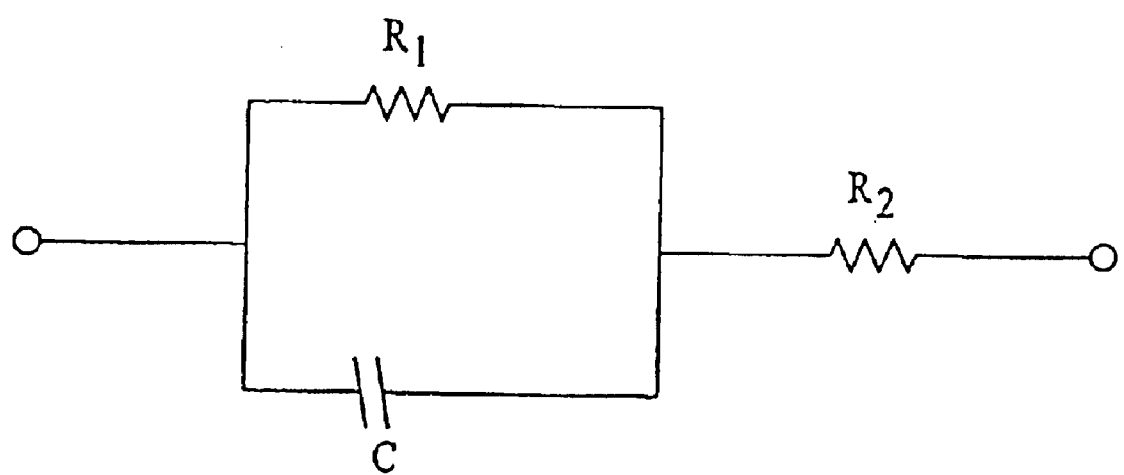
FIG. 1 depicts a schematic of an electrical model for skin.

Preferred embodiments of the present invention and their advantages may be understood by referring to FIGS. 1–14, wherein like reference numerals refer to like elements, and are described in the context of a method and system for conditioning biological cells, tissues, and organs to facilitate enhanced electrical and bioelectrical transmission and reception of electrical potentials and currents.

Overexposure to ultrasound may cause skin damage from increased heat, increased pressure and other factors. Skin tissue can be modeled using an R-C circuit similar to that shown in FIG. 1. The "skin circuit," shown in the figure, consists of a resistor $R_1$ in parallel with a capacitor C, both of which are in series with a resistor $R_2$. For normal, intact skin, of an area of about 1.7 $cm^2$, the value for $R_1$ is about 100 k$\Omega$, the value for C is about 13 $\mu$F and the value for $R_2$ is about 2 k$\Omega$. Of course, these values will vary from person to person depending on skin type and condition. By its nature, the behavior (i.e., the frequency response) of the "skin circuit" changes in response to different excitation frequencies. For example, under normal conditions, the impedance of this circuit will decline sharply as frequency increases, for example, from 10 Hz to 1 kHz. That is, at low frequencies, the capacitive component of the impedance of the parallel combination of $R_1$ and C is significant and therefore the overall impedance of the circuit is high. At higher frequencies, however, the capacitive component to the impedance of the parallel combination decreases and, therefore, the overall impedance of the "skin circuit" declines.

Skin permeability can be derived from the measurements of one or more various electrical parameters of the skin, e.g., impedance, conductance, inductance, and capacitance. Particularly, the value of $R_1$ significantly decreases as the skin becomes permeable. For example, $R_1$ may drop to a value around 5 k$\Omega$ for a skin area of about 1.7 $cm^2$. Therefore, the frequency response of the overall skin circuit becomes much flatter as frequency increases. That is, the difference between the impedance of the circuit at 10 Hz and 1 kHz would not be nearly as significant as at 10 Hz alone. The methods and systems of the present invention measure skin permeability by measuring one or more electrical parameters of an area of skin while that is being exposed to ultrasound. The source of the ultrasound is adjusted based on the measured electrical parameters in order to achieve and/or not exceed a desired skin permeability.

Figure 2:
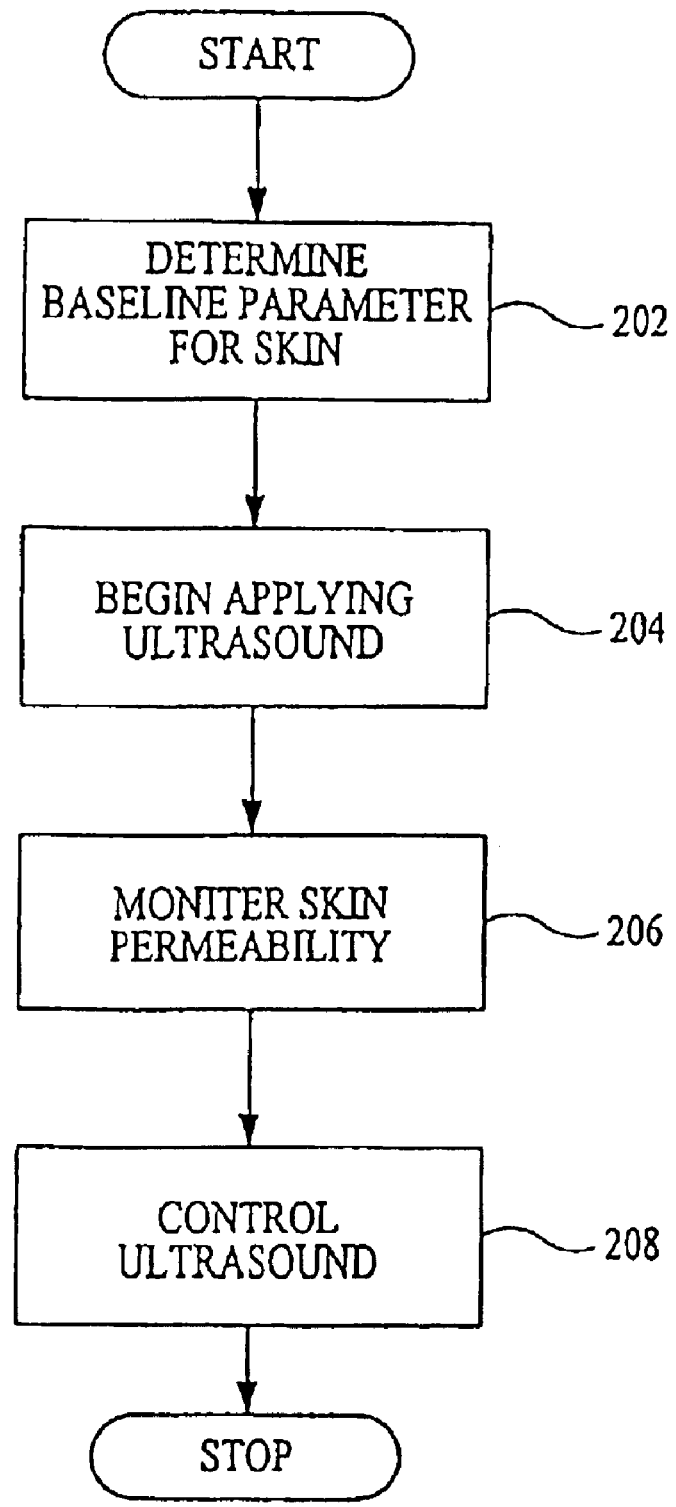
FIG. 2 depicts a flow chart of a method for controlled application of ultrasound according to one embodiment of the invention.

According to one embodiment of the present invention, a method for controlled enhancement of skin permeability is disclosed, and will be explained in conjunction with FIG. 2. Typically, when a skin permeabilizing device, such as an ultrasonic device, is used to enhance transdermal transport properties, the skin permeabilizing device is applied to a relatively small area of skin. In step 202, a baseline measurement for some electrical parameter is determined for the area of skin to which the skin permeabilizing will be applied to determine baseline parameters. In one embodiment, a baseline impedance is measured for the area of skin to which the skin permeabilization device is to be applied. In other embodiments, a baseline conductance, a baseline capacitance, a baseline inductance, or a baseline capacitance may be measured.

The baseline measurement is preferably made by using two or more electrodes. As is shown in greater detail in FIG. 3, an electrode, such as source electrode 310, is coupled to the area of skin to which ultrasound is to be applied. Source electrode 310 does not have to make direct contact with the skin. Rather, it may be electrically coupled to the skin through the medium that is being used to transmit ultrasound. A second or counter electrode, such as conductive band 312, may be positioned on a second area of skin that the skin permeabilizing device will not be applied to. This second area of skin can be adjacent to the area of skin to which the skin permeabilizing device will be applied, or it can be distant from that area of skin.

In one embodiment, the ultrasonic transducer and horn that apply the ultrasound double as the source electrode through which electrical parameters of the area of skin may be measured, and is coupled to the skin through a conductive solution, such as saline, used as an ultrasound medium. In another embodiment, a separate electrode may be affixed to the area of skin that ultrasound will be applied to and is used as the source electrode. In still another embodiment, the housing of the device used to apply ultrasound to the area of skin may be used as the source electrode. The electrode can be made of any suitable conducting material including, for example, metals and conducting polymers.

When the two electrodes are properly positioned, the baseline measurement may be made by applying an electrical signal to the area of skin through the electrodes. The electrical signal supplied preferably has a sufficient intensity so that the electrical parameter of the skin can be measured, but a suitably low intensity so that the electrical signal does not cause damage to the skin or any significant detrimental effects. In one embodiment, an alternating current (AC) source with a frequency between 10 and 100 Hz is used to create a voltage differential between the source electrode and the counter electrode. In order to avoid a risk of permanent damage to the skin, the voltage supplied does not exceed 500 mV, and, preferably, does not exceed 100 mV. In another embodiment, the current can also be similarly limited. The baseline measurement is made after the source has been applied using appropriate circuitry, the implementation of which is apparent to one of ordinary skill in the art. In one embodiment, a resistive sensor is used to measure the impedance of the area of skin at a frequency between 10 to 100 Hz. In another embodiment, a 1 kHz source is used. Sources of other frequencies are also possible. In other embodiments, the circuitry may have multiple circuits for switching between measuring impedance, capacitance, inductance, and/or conductance.

Referring again to FIG. 2, in step 204, the skin permeabilizing device, such as an ultrasound providing device, is applied to the area of skin. Although the exact ultrasound parameters are not the subject of this invention, according to one embodiment using an ultrasonic device as a skin permeabilizing device, ultrasound having a frequency of about 55 kHz, and an intensity of about 10 W/cm$^2$ may be used to enhance the permeability of the area of skin to be used for transdermal transport.

After the skin permeabilizing device has been turned on, in step 206 the permeability of the area of skin is monitored. More specifically, and as discussed above, electrical parameters of the area of skin are used as a proxy for skin permeability. That is, what is actually being monitored is the electrical parameter for which a baseline measurement was made in step 202. The monitoring measurements are made using the same electrode set up that was used to make the baseline measurement.

In step 208, the skin permeabilizing device is controlled based on the monitoring measurements made in step 206. In one embodiment, the monitoring measurements are fed back to a microcontroller that is used to control the skin permeabilizing device. When ultrasound is used, the permeability enhancement obtained by supplying ultrasound is limited. That is, once a certain permeability is reached, the further application of ultrasound will not further enhance skin permeability. Overexposure to ultrasound, or cavitation caused thereby, may result in damage to the skin from localized pressure, temperature increases, and shear stresses. Therefore, in one embodiment, when the parameter being monitored reaches its predetermined value, the ultrasound-producing device is turned off. If the parameter being monitored has not reached the predetermined value, the measurement is repeated until the predetermined value is reached.

The predetermined value may depend upon a number of factors including the skin characteristics of the individual and the frequency of the excitation source. As is apparent to one of ordinary skill in the art, a specific correlation between the electrical parameter being used and skin permeability may be determined by conducting experiments and using experimental data. The predetermined value may then be determined on a subject-by-subject basis, taking into account all appropriate factors and the empirical data.

According to another embodiment, the intensity of the skin permeabilizing device may be gradually scaled back as the point of maximum permeability enhancement is approached. In one embodiment, as the parameter being monitored reaches 50% of the predetermined value, either the intensity or the duty cycle may be reduced by a predetermined amount, such as 50%. This is done so that the predetermined value is not "overshot," thereby increasing the risk of skin damage. Additional controls are possible. For example, in another embodiment, the intensity may be scaled back when the parameter being monitored reaches 25%, 50% and 75% of the predetermined value.

According to another embodiment, permeability enhancement control may be accomplished using two electrical sources having different frequencies. This method relies on the observation, discussed above, that as the skin becomes more permeable, the frequency response of the skin becomes flatter. In this embodiment, the initial step 202 of measuring a baseline for the parameter is unnecessary because the ultrasound control is based on a differential between the parameter value at two different frequencies of excitation. Nevertheless, a baseline measurement may still be desirable in order to determine the range of values to expect. In this embodiment, the electrode arrangement may be the same as that described above. And, step 204 of beginning ultrasound application is also the same as recited above. Thus, the details of these steps will not be reiterated.

After the skin permeabilizing has begun, in step 206, skin permeability is monitored. In this embodiment, skin permeability is also monitored using an electrical parameter measured from the skin as a proxy. This embodiment differs from the first embodiment in that the electrical parameter is measured at two frequencies. In one embodiment, the impedance of the skin is measured at frequencies of 10 Hz and 1 kHz. These measurements are then used to control the skin permeabilizing device.

According to this embodiment, in step 208 the parameter measurement at a first frequency is compared with the parameter measurement at a second frequency to determine whether the two measurements are within a predetermined differential. If the two values are within a predetermined differential, it provides an indication that the frequency response of the skin has flattened and, therefore, is an indication that the skin has reached an enhanced level of permeability. At this point, the skin permeabilizing device is turned off. In one particular embodiment, an impedance of the skin is measured at 10 Hz and at 1 kHz. And, if the two impedance measurements are within 20% of each other, the skin permeabilizing device may be turned off.

The rate of change in the parameter measurements may also be used to determine a point at which the skin permeabilizing device is scaled back or discontinued. The rate of change of one, or both, of the parameters may be used. In another embodiment, the rate of change of the difference between the two parameters may also be used. As the rate of change reaches a predetermined value, the intensity of the skin permeabilizing device may be gradually scaled back or discontinued, in a manner similar to that discussed above.

In a modification of this embodiment, the intensity of the skin permeabilizing device may be gradually scaled back as the point of maximum permeability enhancement is approached. For example, as the differential between the two parameter measurements approaches 50% of the predetermined differential value, either the intensity or the duty cycle may be reduced by a predetermined amount, such as 50%. Additional controls are possible. For example, in another embodiment, the intensity is scaled back when the differential between the two parameters being monitored reaches 25%, 50% and 75% of the predetermined differential value.

The methods described above use a single electrical parameter to control the ultrasound-producing device. Nevertheless, control of the ultrasound-producing device may also be based on two or more electrical parameters.

Figure 3A:
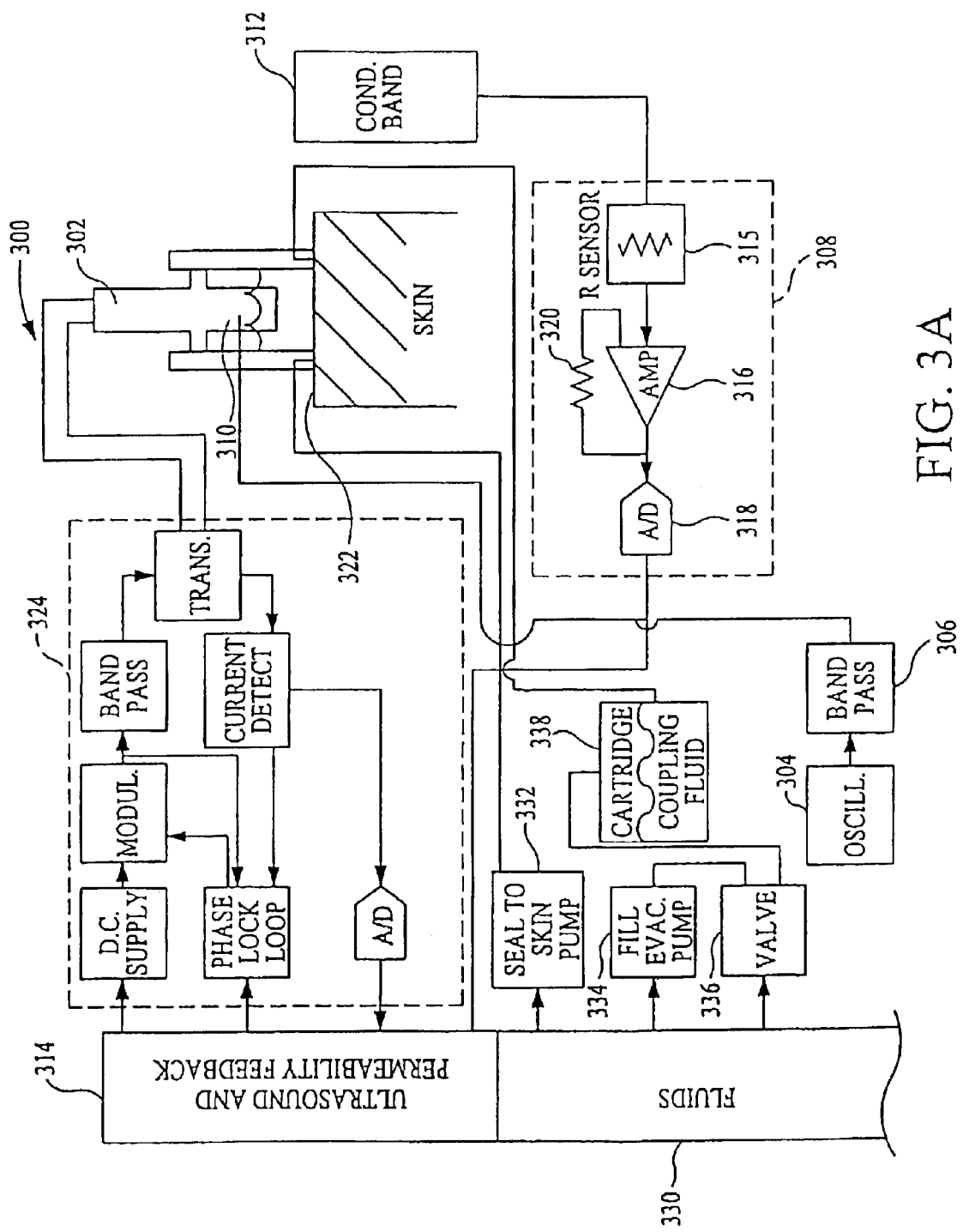
FIG. 3 depicts a diagram of a circuit that enhances skin permeability and monitors enhancement of skin permeability according to one embodiment of the invention.
Figure 3B:
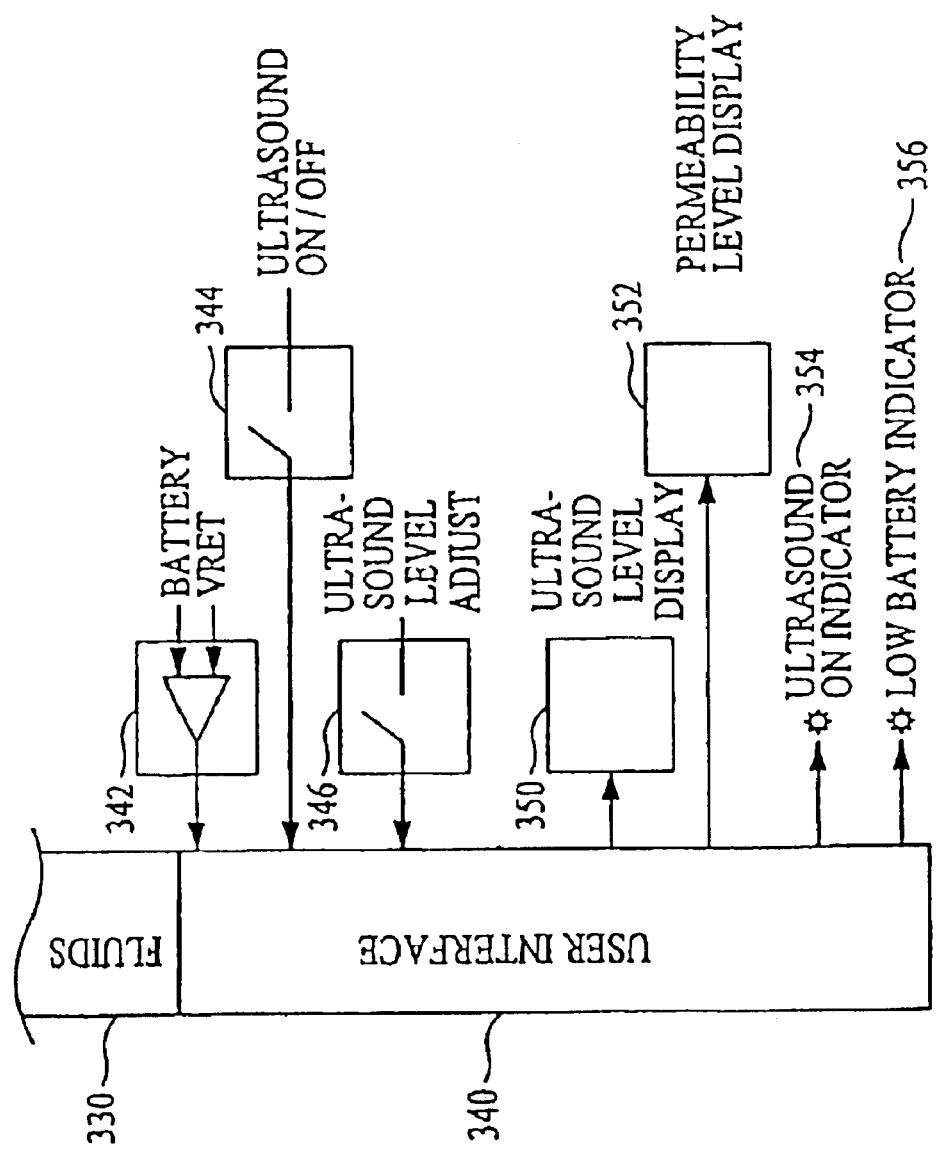

According to another embodiment of the present invention, an apparatus for controlled ultrasound 300 is described in conjunction with FIG. 3. Apparatus 300 uses an ultrasound-producing device as the skin permeabilizing device; it should be noted that other devices for increasing the skin permeability may be used in place of the ultrasound-producing device. For example, the permeability of the skin may be increased through the application of electromagnetic fields, chemicals, mechanical forces, needles, thermal ablation, laser ablation, etc.

Apparatus 300 includes ultrasound transducer/horn combination 302, source 304, bandpass filter 306, permeability monitoring circuit 308, source electrode 310, return electrode 312, and microcontroller 314. Permeability monitoring circuit 308 comprises current sensor 315, amplifier 316, analog to digital (A/D) converter 318, and resistor 320.

Ultrasound transducer/horn combination 302 is used to apply ultrasound to the area of skin 322. Transducer 302 may be any known ultrasound transducer, such as a piezoelectric transducer, a ceramic transducer, or polymer block transducer. The horn can have any known configuration. In one embodiment the horn is made of a conductive metal.

As described above, while the ultrasound is being supplied to the area of skin, it is important to monitor the skin permeability and control the ultrasound application so that the skin will not be overexposed to ultrasound. Apparatus 300 may include the electrical control circuitry elements described above in order to accomplish this monitoring and control. Specifically, source 304 and bandpass filter 306 are provided to drive the electrical control circuitry. That is, in order to obtain the electrical parameter measurements used for controlling source 304, a small signal is passed through the area of skin. In one embodiment of the present invention, source 304 provides a 10 Hz AC square wave voltage that is used to monitor the permeability of the area of skin in apparatus 300. Bandpass filter 306 is provided to convert the square wave into a sinusoid.

Source electrode 310 and return electrode 312 provide an electrical path through which electrical parameters of the area of skin 322 can be measured. Source electrode 310 may be incorporated into transducer/horn combination 302, and is preferably formed of any suitable conductive material. In one embodiment, the ultrasound horn is metal and is used as the source electrode. Return electrode 312 is a conductive band and is preferably formed from a conductive polymeric path or a metallic foil.

Permeability monitoring circuit 308 comprises circuitry designed to measure an electrical parameter of the skin as a proxy for the permeability of the skin. More specifically, according to one embodiment of the present invention, permeability monitoring circuit 308 comprises circuitry designed to measure the current flow through the area of skin 322 and to convert that measurement in to a form suitable for use by microcontroller 314. Permeability monitoring circuit 308 comprises current sensor 315 that is operable to measure the impedance of area of skin 322. Current sensor 315 may be any sensor that may be used to measure current, and, in one embodiment, current sensor 315 is a 1 kΩ current sense resistor where the output voltage generated is 1000 times the current flowing through the skin. The output of current sensor 315 is an analog signal that should be digitized before it may be used by microcontroller 315. Amplifier 316 and resistor 320 serve to amplify the output voltage of current sensor 315 so that it may be digitized by A/D converter 318. AID converter 318 may be any suitable A/D converter.

The signal from A/D converter 316 may then be provided to microcontroller 314. Microcontroller 314 may be any suitable microcontroller. Microcontroller 314 is programmed to control transducer driver circuit 324 as described above. In one embodiment, microcontroller 314 determines whether the signal from permeability monitoring circuit 308 is greater than some predetermined value. If so, microcontroller 314 may turn off the ultrasound by, for example, shutting off the direct current (DC) supply for transducer driver circuit 324. Microcontroller 314 may also be configured to provide other controls, such as altering the duty cycle of transducer driver circuit 324 through the phase lock loop circuit.

According to one embodiment of the present invention, additional controls and a user interface may be provided. Fluids controller 330 controls the pumps and fluids for the system. Pump 332 may be provided to provide a seal between transducer 302 and the surface of skin 322. Pump 334, in conjunction with valve 336, may be used to fill and evacuate the chamber of transducer 302. The coupling fluid used in transducer 302 may be provided in cartridge 338. Other devices and methods for providing coupling fluid may also be used.

A user interface may also be provided. For example, user interface 340 includes a low battery sensor 342, which may include a comparator or similar level-sensing circuit. Switch 344 may be provided to turn on or off the ultrasound-producing device. Input 346 may be provided to allow a user to adjust the ultrasound intensity. The ultrasound level may be provided in display 350. The permeability level of the skin may be provided in display 352. Visual and/or audio indicators, such as indicators 354 and 356 may be provided to alert the user of the operation of the ultrasound, as well as a when there is a low battery. Additional controls and displays may be provided, as required, to prevent a user from applying ultrasound of a harmful intensity or duration, or to prevent ultrasound from being applied before the system is ready (i.e., before coupling fluid is provided for transducer 302, etc.).

Figure 4:
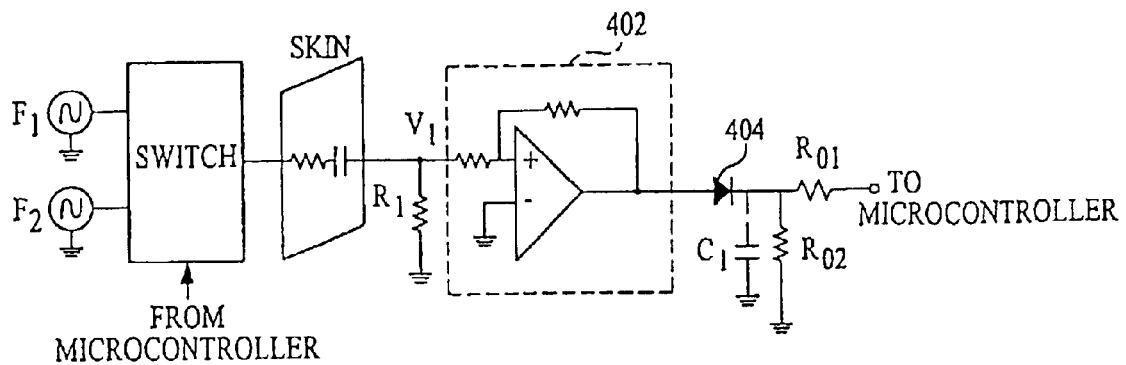
FIG. 4 depicts a permeability monitoring circuit according to another embodiment of the invention.

The circuitry described above may be replaced with other elements if the electrical parameter measurements are accomplished in a different way. More specifically, the circuitry shown in FIG. 4 or FIG. 5 could be used in place of source 304, bandpass filter 306, and permeability monitoring circuit 308 if the aforementioned control methodology using sources at two frequencies is used. FIG. 4 schematically depicts one embodiment of a circuit useful for implementing such dual frequency control of skin permeability. The circuit comprises sources $F_1$ and $F_2$ that supply two distinct AC signals to the area of skin to which ultrasound is being applied. In one embodiment, sources $F_1$ and $F_2$ comprise a 10 Hz and a 1 kHz current source respectively. These sources are alternately applied to the area of skin through a microprocessor controlled switch. In the embodiment shown in FIG. 3, microcontroller 314 would control the switch so that sources $F_1$ and $F_2$ alternately excite the skin.

After excitation by one of the sources, the impedance of the skin is measured by measuring the voltage $V_1$. That is, $V_1$ is transmitted to a microprocessor (e.g., microcontroller 314 in FIG. 3) through gain circuit 402, diode 404, capacitor $C_1$, and output resistors $R_{O1}$ and $R_{O2}$. The combination of diode 404 and capacitor $C_1$ comprises an AC to DC converter suitable for input to an A/D converter to transform the analog signal from gain circuit 402 to a digital signal suitable for use by a microprocessor. Output resistors $R_{O1}$ and $R_{O2}$ provide impedance matching and filtering for the microprocessor, respectively.

In operation, the circuit of FIG. 4 in conjunction with a suitably programmed microcontroller alternately applies a 10 Hz and a 1 kHz AC source to the skin. The circuit, in conjunction with the microprocessor, measures the impedance of the skin at both frequencies. The microcontroller makes suitable adjustments to the ultrasound-producing device based on the differential between the impedance of the skin at 10 Hz and the impedance of the skin at 1 kHz, as previously explained.

Figure 5:
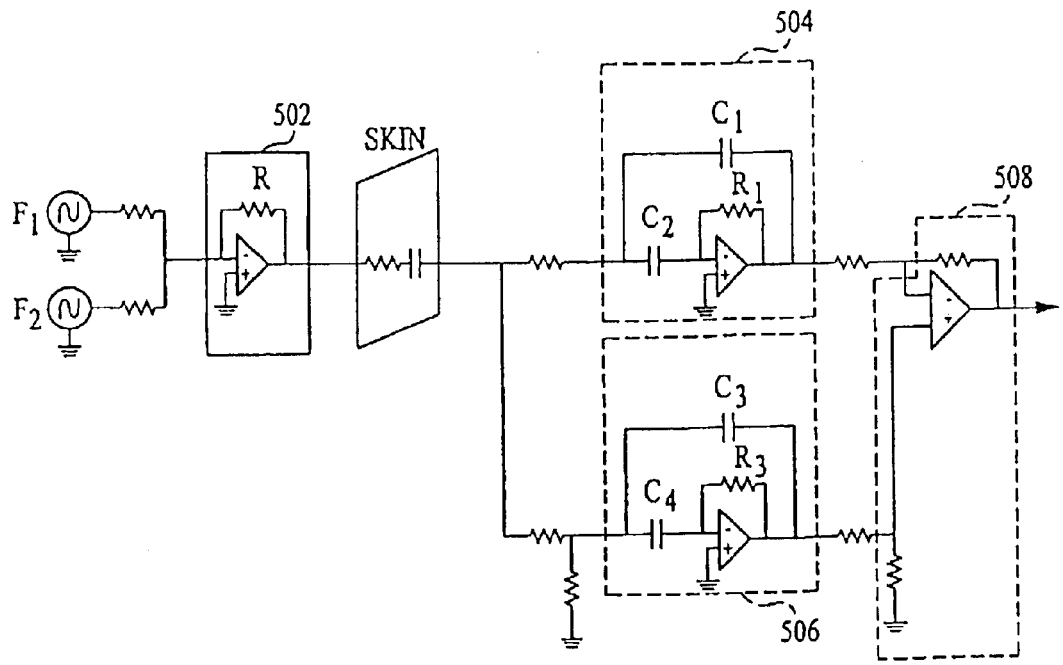
FIG. 5 depicts a permeability monitoring circuit according to one embodiment of the invention.

FIG. 5 schematically depicts yet another embodiment of permeability monitoring circuit for use with multiple frequency excitation. In the circuit of FIG. 5, sources $F_1$ and $F_2$ are applied simultaneously through adder circuit 502 to the area of skin to which ultrasound is being applied. The output signal from the skin is then fed to two bandpass filters 504 and 506. Elements $C_1$, $C_2$ and $R_1$ of bandpass filter 504 are preferably chosen to create a pass band centered around the frequency of source $F_1$. Elements $C_3$, $C_4$ and $R_2$ of bandpass filter 506 are preferably chosen to create a pass band centered around the frequency of source $F_2$. The output signals from bandpass filters 504 and 506 are then subtracted in comparator circuit 508 to create a differential signal for the microprocessor. A suitably configured microprocessor then uses this differential signal to make suitable adjustments to the ultrasound-producing device.

According to another embodiment of the present invention, an apparatus and method for regulating the degree of skin permeabilization through a feedback system is provided. This apparatus and method may be similar to what has been described above, with the addition of further regulation of the degree of skin permeabilization. In this embodiment, however, the application of the skin permeabilizing device is terminated when desired values of parameters describing skin conductance are achieved. As the discussion proceeds with regard to FIG. 6, it should be noted that the descriptions above may be relevant to this description.

Figure 6:
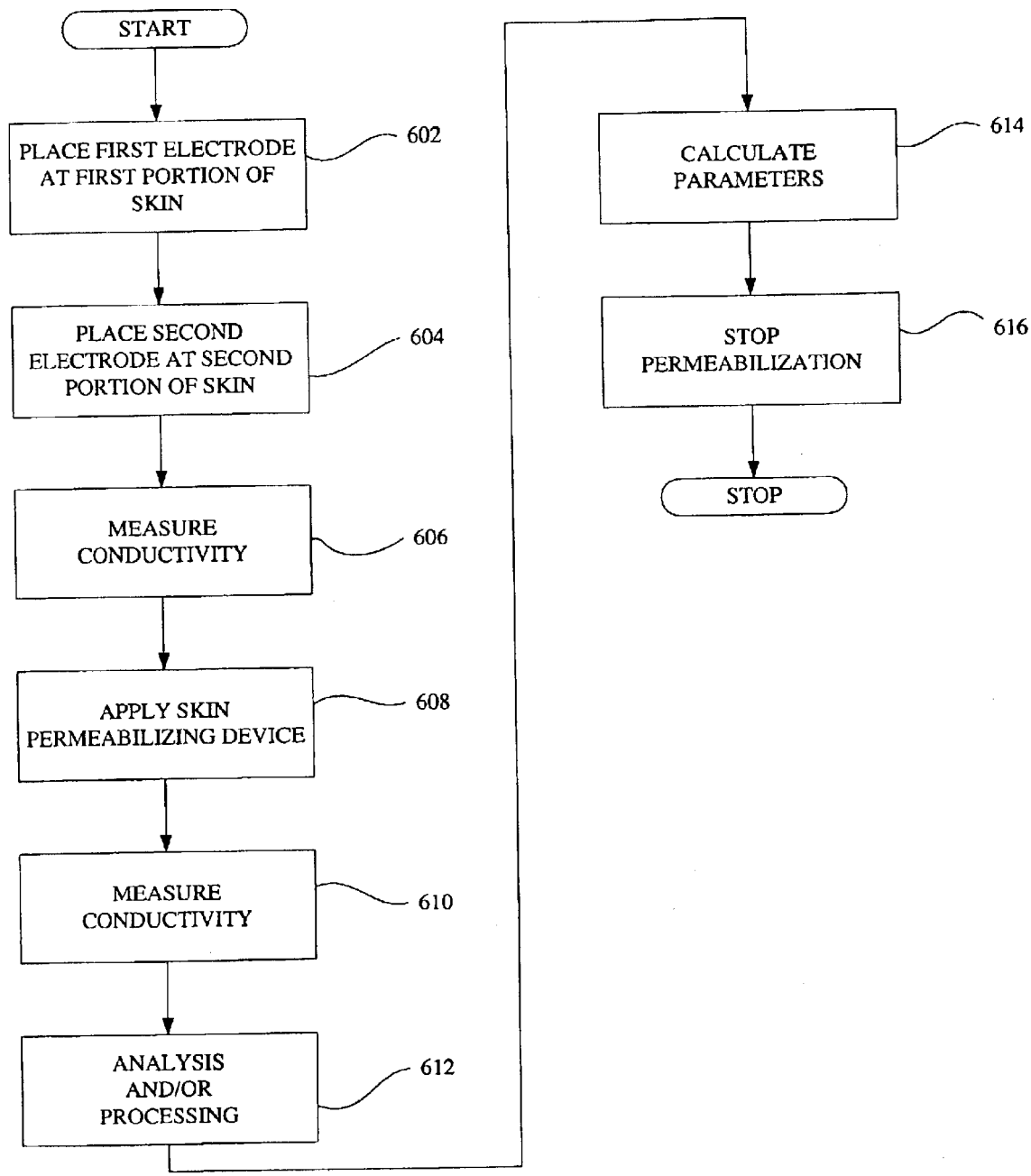
FIG. 6 depicts a flow chart of a method for controlled application of ultrasound according to one embodiment of the invention.

Referring to FIG. 6, a flowchart of the method is provided. In step 602, a first, or source, electrode is coupled in electrical contact with a first area of skin where permeabilization is required. As discussed above, the source electrode does not have to make direct contact with the skin. Rather, it may be electrically coupled to the skin through the medium that is being used to transmit ultrasound. In one embodiment, where an ultrasound-producing device is used as the skin permeabilizing device, the ultrasonic transducer and horn that will be used to apply the ultrasound doubles as the source electrode through which electrical parameters of the first area of skin may be measured and is coupled to the skin through a saline solution used as an ultrasound medium. In another embodiment, a separate electrode is affixed to the first area of skin and is used as the source electrode. In still another embodiment, the housing of the device used to apply ultrasound to the first area of skin is used as the source electrode, or the housing may hold the source electrode. The source electrode can be made of any suitable conducting material including, for example, metals and conducting polymers.

Next, in step 604, a second, or counter, electrode is coupled in electrical contact with a second area of skin at another chosen location. This second area of skin can be adjacent to the first area of skin, or it can be distant from the first area of skin. The counter electrode can be made of any suitable conducting material including, for example, metals and conducting polymers.

When the two electrodes are properly positioned, in step 606, an initial conductivity between the two electrodes is measured. This may be accomplished by applying an electrical signal to the area of skin through the electrodes. In one embodiment, the electrical signal supplied may have sufficient intensity so that the electrical parameter of the skin can be measured, but have a suitably low intensity so that the electrical signal does not cause permanent damage to the skin, or any other detrimental effects. In one embodiment, an AC source of frequency between 10 to 100 Hz is used to create a voltage differential between the source electrode and the counter electrode. The voltage supplied should not exceed 500 mV, and preferably not exceed 100 mV, or there will be a risk of damaging the skin. The current magnitude may also be suitably limited. The initial conductivity measurement is made after the source has been applied using appropriate circuitry. In another embodiment, a resistive sensor is used to measure the impedance of the area of skin at a frequency between 10 and 100 Hz. In another embodiment, both measurements, or multiple measurements may be made using similar or dissimilar stimuli. Sources of other frequencies are also possible.

In step 608, a skin permeabilizing device is applied to the skin at the first site. Any suitable device that increases the permeability of the skin may be used. In one embodiment, ultrasound is applied to the skin at the first site. According to one embodiment, ultrasound having a frequency of 55 kHz and an intensity of about 10 W/cm$^2$ is used to enhance the permeability of the area of skin to be used for transdermal transport, although it will be readily understood that other frequencies and power levels may be implemented.

In step 610, the conductivity between the two sites is measured. The conductivity may be measured periodically, or it may be measured continuously. The monitoring measurements are made using the same electrode set up that was used to make the initial conductivity measurement.

In step 612, mathematical analysis and/or signal processing may be performed on the time-variance of skin conductance data. Experiments were performed on human volunteers according to the procedure above, with ultrasound used as the method of permeabilization. Ultrasound was applied until the subjects reported pain. Skin conductivity was measured once every second during ultrasound exposure. After plotting the conductance data, the graph resembled a sigmoidal curve, which can be represented by the following general sigmoidal curve equation:

$$C = Ci + \frac{(C_f - C_i)}{1 + e^{-S(t - t^*)}}$$

where C is current; $C_i$ is current at t=0; $C_f$ is the final current; S is a sensitivity constant; $t^*$ is the exposure time required to achieve an inflection point; and t is the time of exposure.

Figure 7:
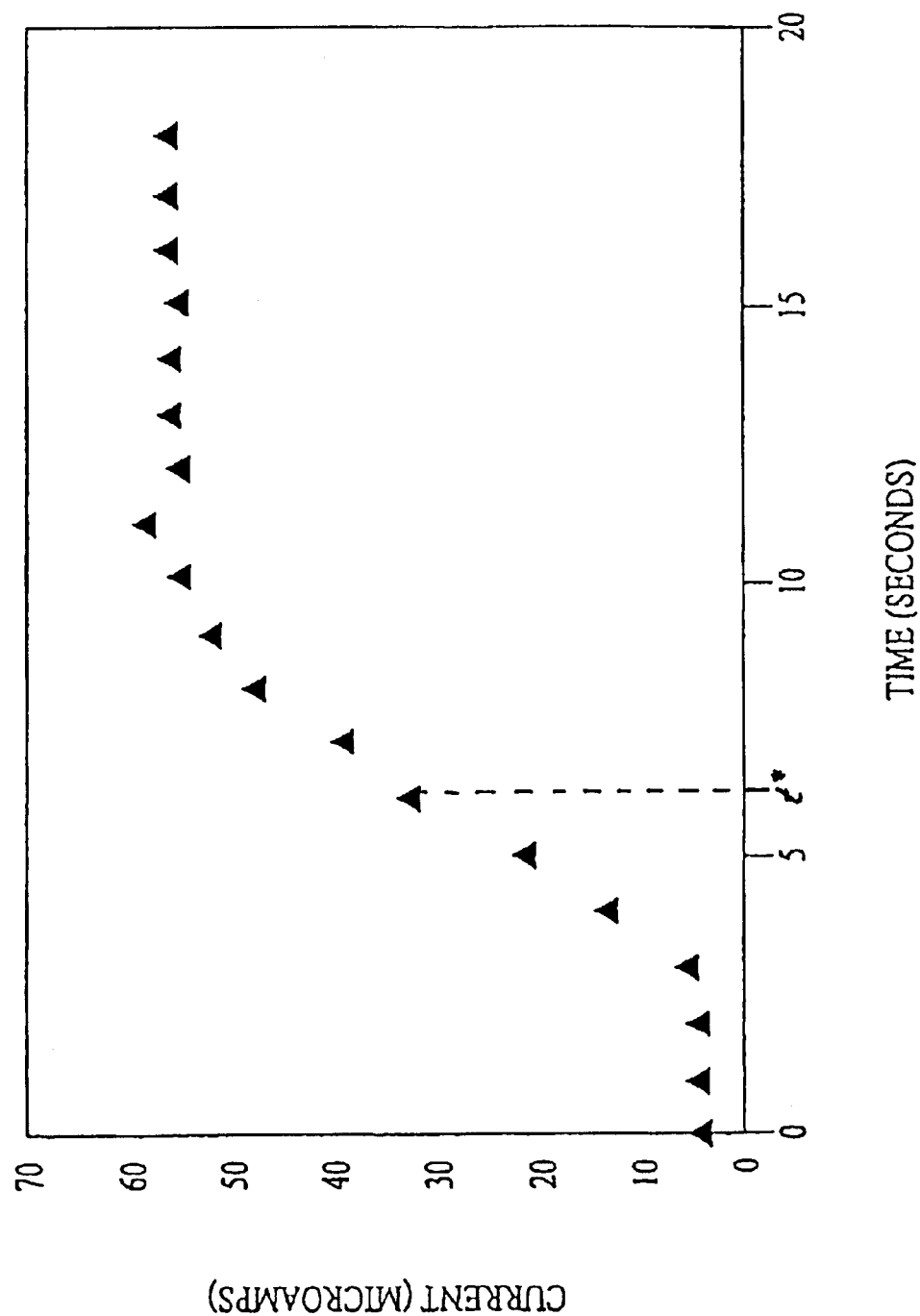
FIG. 7 depicts the time variation of the skin conductance while being exposed to ultrasound.

The data from the tests were plotted in FIG. 7, which is a plot of current over time. FIG. 7 demonstrates the time variation data of skin conductance while being exposed to ultrasound. As noted before, the data points fall along a sigmoidal curve and can be fitted to the above equation. As shown in the plot, the value of t*, which corresponds to the exposure time required to achieve an inflection point (i.e., a point where the slope of the curve changes sign), approximately indicates the time required to achieve half the total exposure.

Figure 8:
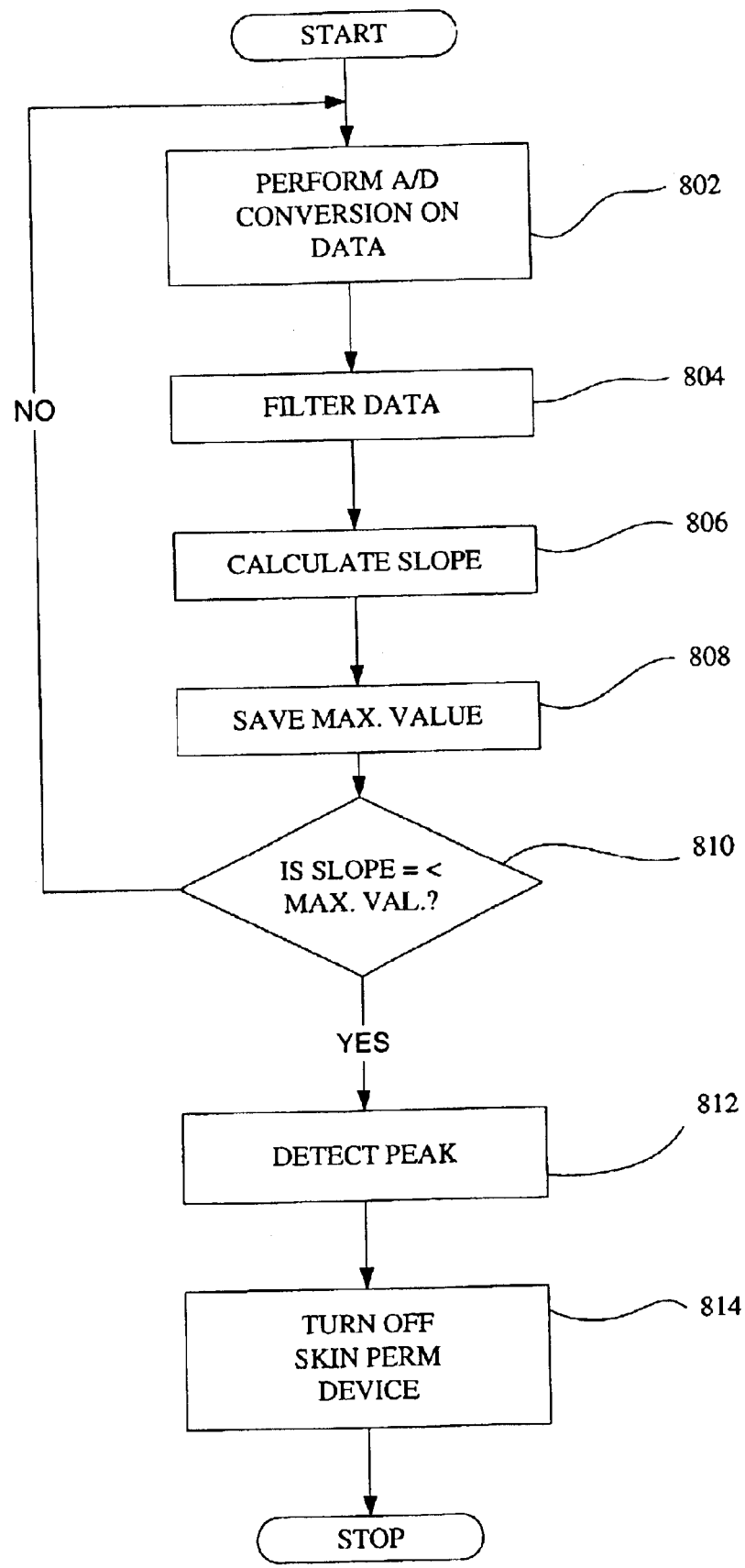
FIG. 8 depicts a flowchart of a method of determining when to terminate the application of ultrasound according to an embodiment of the invention.
Figure 9A:
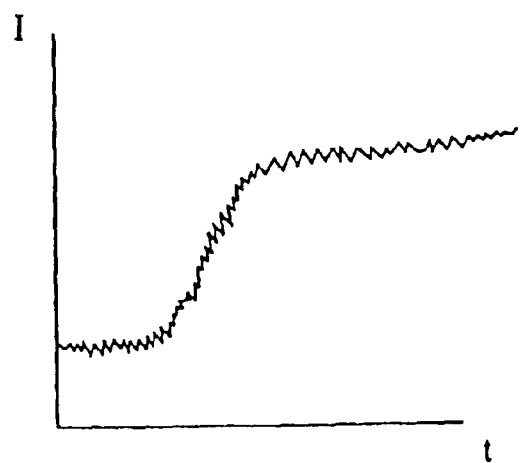
FIG. 9 depicts example graphs of the method of FIG. 8.
Figure 9B:
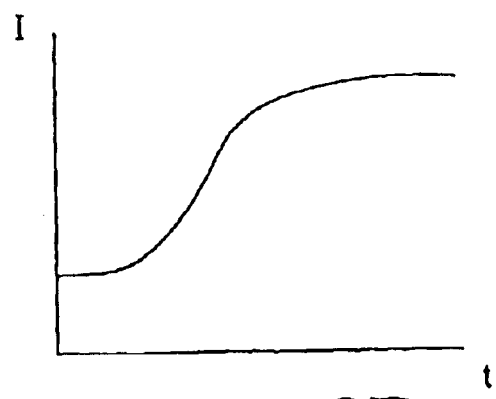
Figure 9C:
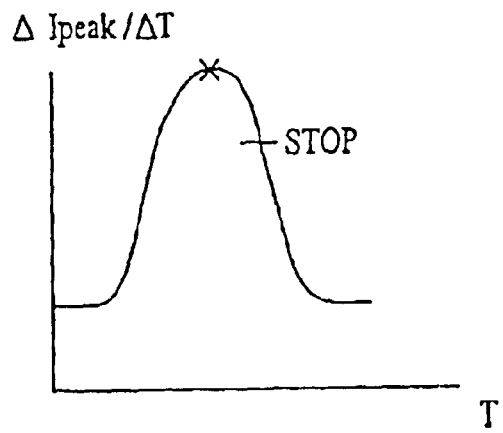

Referring to FIGS. 8 and 9, a flowchart depicting a method of determining when to terminate the application of ultrasound, and corresponding example graphs, are provided. In step 802, an A/D conversion is performed on the conductivity data. This results in a graph similar to the one in FIG. 9A. Next, in step 804, filtering is performed on the digital data. As shown in FIG. 9B, the filtered data has a smoother curve than the unfiltered data of FIG. 9A. Next, in step 806, the slope of the curve is calculated. In step 808, the maximum value for the slope is saved. If the current value for the slope obtained during subsequent measurements is greater than the maximum value that is saved, the maximum value is replaced with the current value. Next, in step 810, if the slope is not less than or equal to the maximum value, the process returns to step 802 to wait for a peak. If the slope is less than or equal to the maximum value, in step 812 the process detects a peak, or point of inflection, shown in FIG. 9C, then, in step 814, terminates the application of ultrasound to the skin.

In one embodiment, the detection of the peak may be validated. This may be provided to ensure that the "peak" detected, in step 812, was not noise, but was actually a peak.

In other embodiments, ultrasound may be applied even after the inflection point is reached. In one embodiment, ultrasound is applied for a predetermined time. This predetermined time may be based on a percentage of the time to reach the inflection point. For example, once the inflection point is reached, ultrasound continues to be applied for an additional 50% of the time it took to reach the inflection point. Thus, if it took 14 seconds to reach the inflection point, ultrasound is applied for an additional 7 seconds. Other percentages may be used, and this percentage may be based on factors including pain threshold and skin characteristics.

In another embodiment, ultrasound is applied until the slope decreases to a certain value. Referring again to FIG. 8, after the inflection point is reached, the slope decreases as ultrasound is applied. Thus, ultrasound may be applied until the slope decreases by a percentage, such as 50%, or to a predetermined value. As above, this determination is flexible and may vary from individual to individual.

In another embodiment, the current at the inflection point is measured, and then a percentage of this current is still applied. For example, if the inflection point is reached at 40 $\mu$amps, an additional 10% of this, for a total of 44 $\mu$amps, may be reached. Again, this determination is flexible and may vary from person to person.

Referring again to FIG. 6, in step 614, the parameters describing the kinetics of skin conductance changes are calculated. These parameters include, inter alia, skin impedance, the variation of skin impedance with time, final skin impedance, skin impedance at inflection time, final current, exposure time to achieve the inflection time, etc.

In step 616, the skin permeabilizing device applied in step 608 is terminated when desired values of the parameters describing skin conductance are achieved.

Figure 10A:
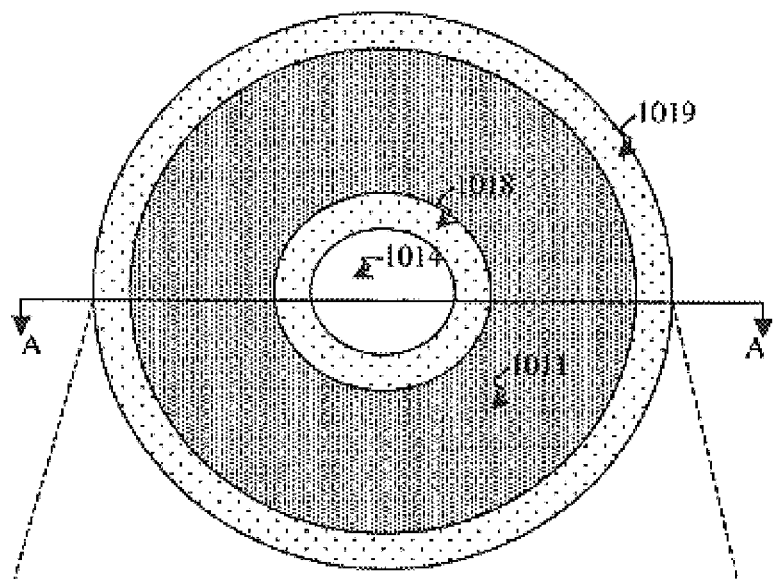
FIG. 10 illustrates a body interface system according to an embodiment of the invention.
Figure 10B:
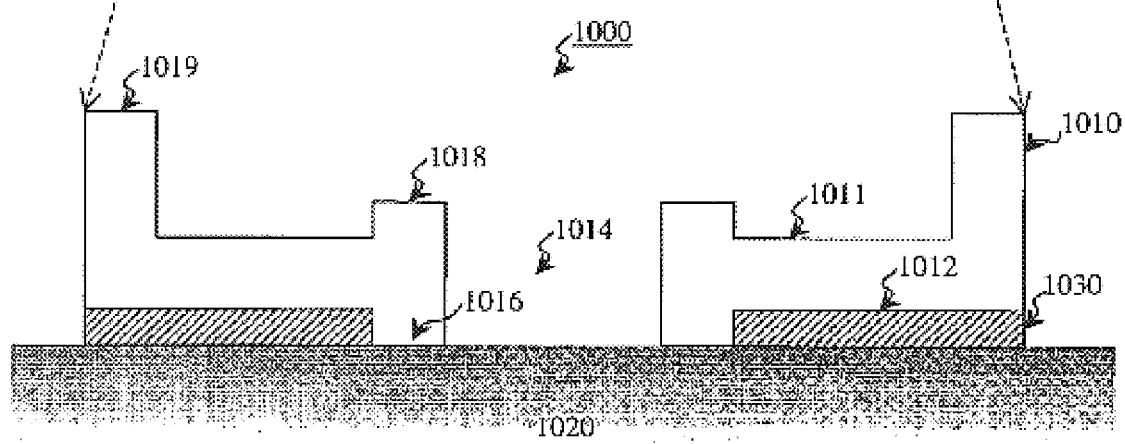

FIG. 10 illustrates a body interface system 1000 for assisting the preparation of a tissue site according to an embodiment of the invention. Particularly, the body interface system 1000 comprises a tissue interface receptacle 1010 placed against a tissue 1020, e.g., skin. FIG. 10A depicts a top view of the tissue interface receptacle 1010 and FIG. 10B depicts a cross-sectional view taken along the cross-section AA. In an exemplary embodiment, the tissue interface receptacle 1010 is a cylindrical or disk shaped rigid member featuring a total thickness of approximately 0.125 inches, an outer diameter of approximately 1.5 inches, and comprises a top surface 1011 and a bottom surface 1012. The bottom surface 1012, which is placed in proximity to the tissue 1020 during use of receptacle 1010, is defined by a concentric circular passage 1014 approximately 0.4 inches in diameter spanning the total thickness of the receptacle 1010. A circular ring 1016 protrudes approximately 0.05 inches outward from the bottom surface 1012. Similarly, a circular ring 1018 preferably protrudes approximately 0.05 inches outward from the top surface 1011, and is located at an end of passage 1014 opposite to the circular ring 1016. The tissue interface receptacle 1010 preferably further comprises a ring shaped outer wall 1019 protruding from the top surface 1011, thereby forming an annular depression of approximately 0.21 inches in depth. The total depth of the tissue interface receptacle 1010 including the outer wall 1019, central disk-shaped portion and circular ring 1016 may be, for example, about 0.385 inches, although deeper and shallower designs may also be used. The tissue interface receptacle 1010 may be constructed from a rigid material such as, but not limited to plastic, which preferably does not cause any discomfort when pressed against the tissue 1020. In another embodiment of the invention, the tissue interface receptacle 1010 may comprise a semi-rigid material such as, but not limited to rubber or an elastomer, which may flex enough to form to a curved contour of the tissue 1020.

In operation, a circular layer of an adhesive 1030 of approximately 0.05 inches thick and preferably covering the entire surface 112 is employed to affix tissue interface receptacle 1010 to the tissue 1020. The adhesive 1030 can comprise a double-sided adhesive tape, sticky gel, or other suitable bonding agent, the identification and implementation of which is apparent to one of ordinary skill in the art, which preferably doesn't damage the tissue 1020 when in place or during removal. The adhesive 1030 temporarily secures the tissue interface receptacle 1010 to the tissue 1020. The circular ring 1016 on the bottom surface 1012 serves to keep the adhesive 1030 from flowing into the passageway 1014. In an alternative embodiment of the invention, an outer circular ring (not shown) can be disposed on the bottom surface 1012 at the perimeter of the tissue interface receptacle 1010 to prevent the adhesive 1030 from escaping during attachment of the receptacle 110 to the skin 1020. The annular depression formed by circular rings 1018 and 1019 is capable of receiving an ultrasound applicator as illustrated in the following figure. Moreover, the passageway 1014 is capable of receiving an electrode device.

One of ordinary skill in the art recognizes that the particular dimensions above relating to the tissue interface receptacle 1010 are exemplary only. Other dimensions and geometric configurations of the interface receptacle 1010 are possible, particularly with respect to those necessary to accommodate various sized and configured ultrasound applicators, electrodes, and/or areas of tissue.

Figure 11:
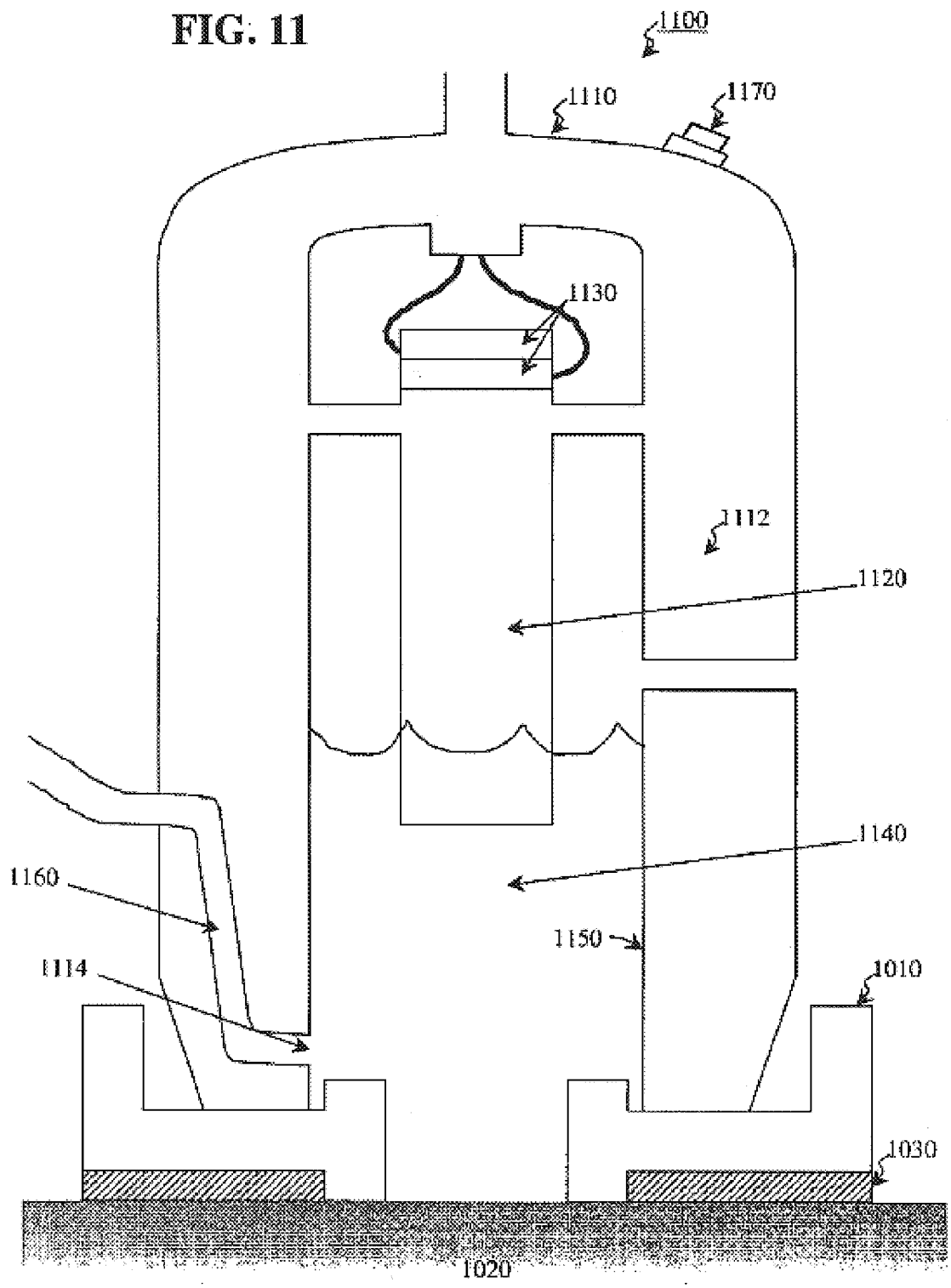
FIG. 11 illustrates an ultrasound applicator according to an embodiment of the invention.

FIG. 11 illustrates an ultrasound applicator system 1100 according to an embodiment of the invention. Particularly, the ultrasound applicator system 1100 comprises an ultrasound applicator 1110 and the tissue interface receptacle 1010. The ultrasound applicator 1110 comprises a generally cylindrical housing 1112 that supports a cylindrical metallic resonator 1120 concentric with the cylindrical housing 1112. The ultrasound applicator 1110 preferably is shaped as an ergonomic hand-held device. Moreover, an on-off button 1170 may be disposed at a convenient location, e.g., top of the cylindrical housing 1112, to be actuated by the thumb of a user.

In an exemplary configuration, the cylindrical housing 1112 features an outer diameter of approximately 1.25 inches, an inner diameter of approximately 0.625 inch, and a length of approximately 4.75 inches for easy gripping by a human hand. The cylindrical housing 1112 is preferably constructed from a rigid material such as plastic. The length and diameter of the resonator 1120 may be selected to accommodate the desired frequency and intensity of ultrasound, as is understood by one of ordinary skill in the art. For example, the length of the resonator 1120 is preferably an integer multiple of a half-wavelength of a chosen excitation ultrasound frequency. Also in a preferred embodiment, the diameter of the resonator 1120 is approximately 0.5 inch.

In a preferred embodiment, the resonator 1120 is excited by piezoelectric transducers 1130 comprising lead zirconate titanate (PZT) placed at the proximal end of resonator 1120. The attachment of the piezoelectric transducers 1130 to a specific location is determined by a nodal position based on the excitation wavelength of the resonator 1120. The resonator 1120 and the transducers 1130 are attached to the cylindrical housing 1112 appropriately so as to minimize loading of the resonator. In an exemplary arrangement, the distance from the distal end of the resonator to the exit of the cylindrical housing is approximately 0.3 inch. Moreover, the clearance of the resonator 1120 with respect to the inner wall of the cylindrical housing 1112 is approximately 0.0625 inch. The cylindrical housing 1112 is capable of making electrical contact with the tissue interface receptacle 1010 and subsequently skin 1020.

In one embodiment of the invention, the cylindrical housing 1112 comprises a port 1114 for the introduction and evacuation of a liquid coupling media 1140 into a chamber 1150 formed, in part, by the cylindrical housing 1112. The coupling media 1140 can be transported via a fluid conduit 1160 into the chamber 1150 using a mechanical syringe or an automatic vacuum pump, the implementation of which is apparent to one of ordinary skill in the art. When the ultrasound applicator 1110 is mated with tissue interface receptacle 1010, the chamber 1150 is capable of receiving the coupling media 1140 without leakage. The ultrasonic applicator 1110 is preferably shaped as an ergonomic hand-held device.

In another embodiment of the invention, the ultrasound applicator 1110 can be applied to the skin without the use of the tissue interface receptacle 1010.

Figure 12:
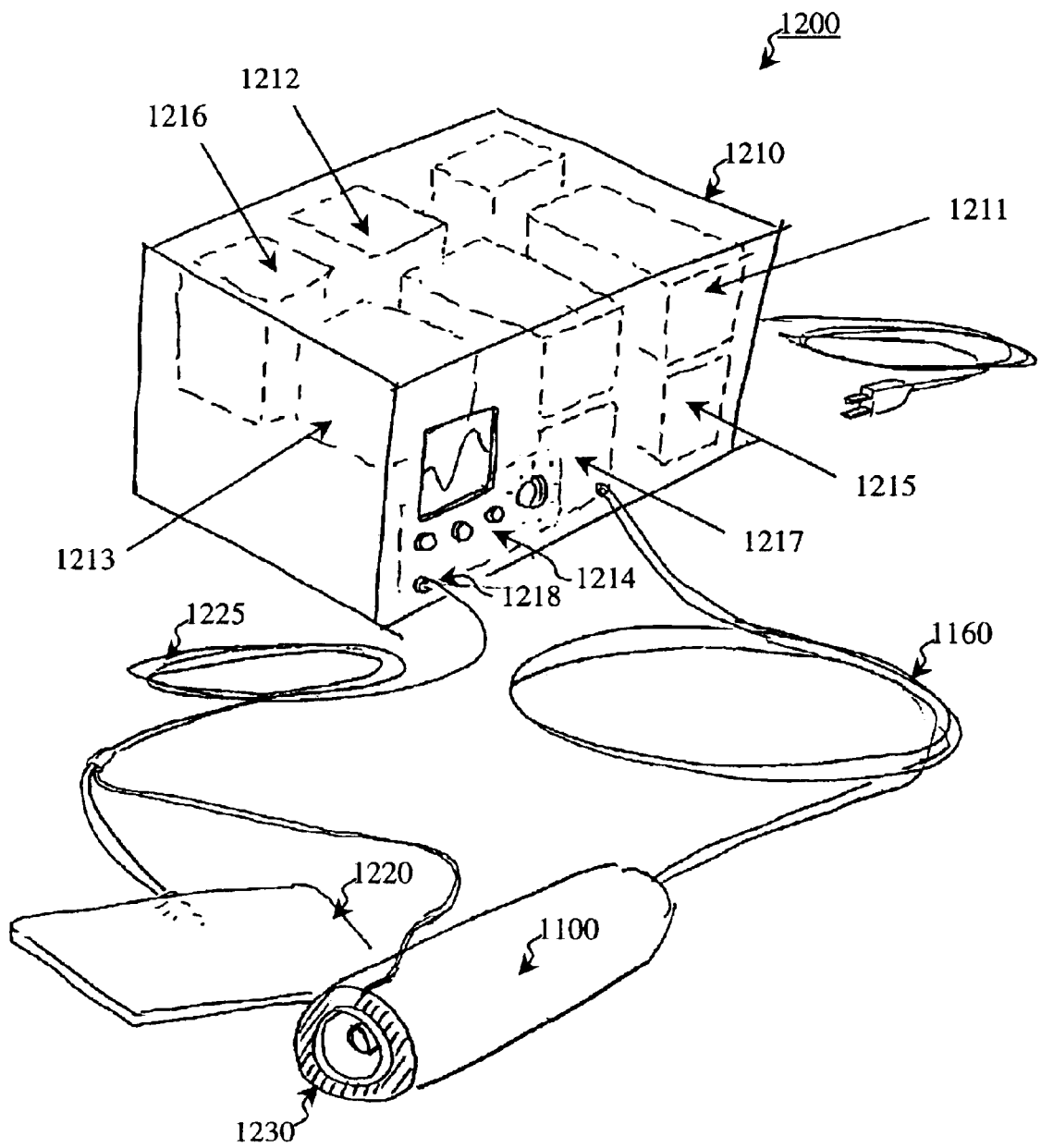
FIG. 12 illustrates a skin preparation system according to an embodiment of the invention.

FIG. 12 illustrates a skin preparation system 1200 according to an embodiment of the invention. Particularly, system 1200 comprises a portable control box 1210, the ultrasound applicator 1110, a reference lead 1220, and a sensing lead 1230. The control box 1210 comprises a power source 1211, a microcontroller 1212, a signal generator 1213, a user interface 1214, a source of coupling media 1215, an optional waste bin 1216, and a pump 1217 for fluid manipulation via the fluid conduit 1160. The power source 1211 may be connected to a permanent or fixed power supply by a power cord 1219. The sensing lead 1230 can be attached to the ultrasound applicator 1110 as illustrated. The control box 1210 also comprises an input/output (I/O) port 1218 for receiving an electrical cable 1225 coupling the reference lead 1220 and the sensing lead 1230 to the I/O port 1218. In an embodiment of the invention, the reference lead 1220 comprises a reusable and rectangular stimulating electrode. In another embodiment, the sensing lead 1230 may be routed to pass through or along the fluid conduit 1160, or may be otherwise separated from the electrical cable 1225 that couples to the reference lead 1220. In another embodiment, the various parts of the skin preparation system 1200, such as the electrical components, leads and cables may be shielded to inhibit radio-frequency interference with one another and with other appliances.

Figure 13:
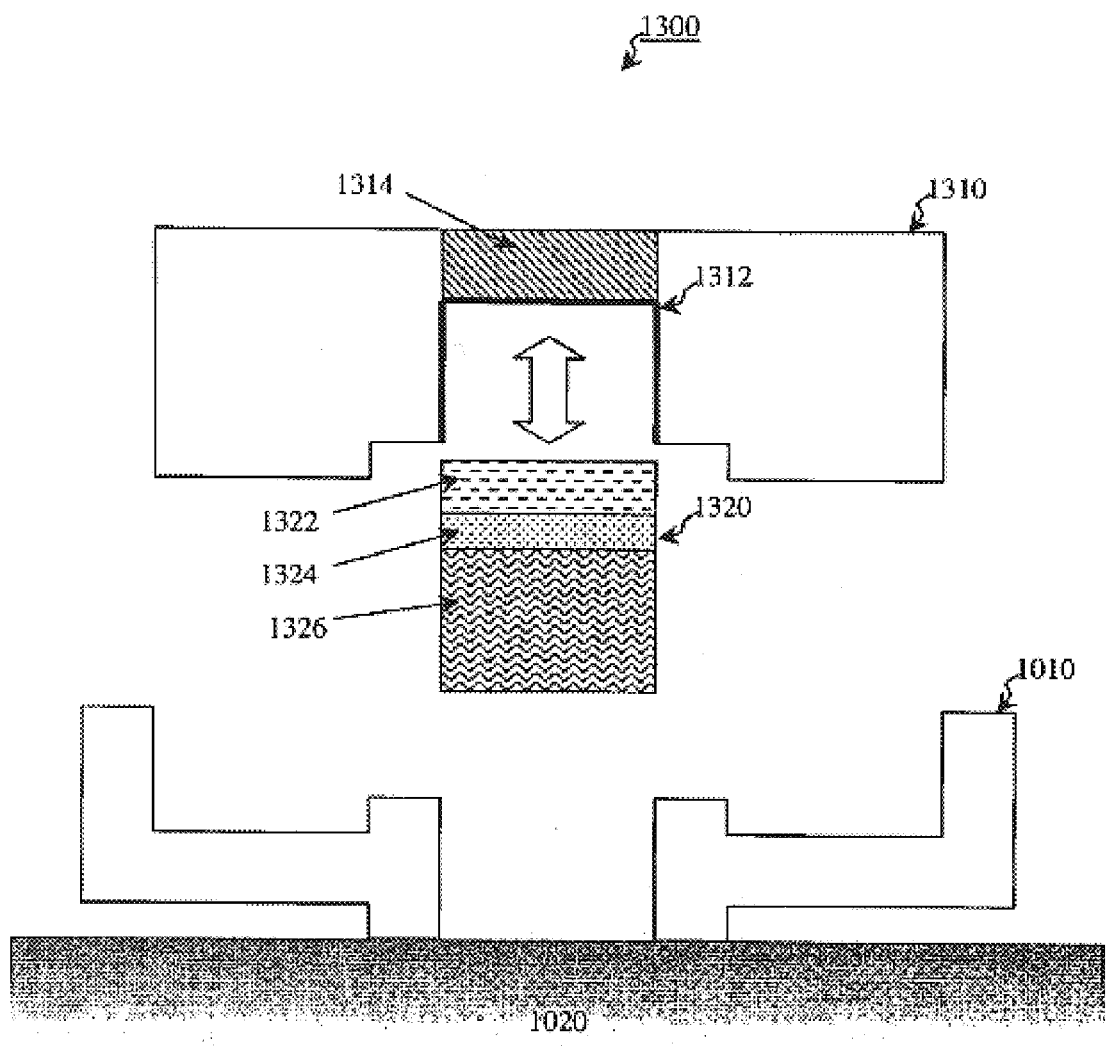
FIG. 13 illustrates an electrode device according to an embodiment of the invention.

FIG. 13 illustrates an electrode device 1300 according to an embodiment of the invention. Particularly, the electrode device 1300 comprises an electrical lead 1310 for optional attachment to the tissue interface receptacle 1010 after skin preparation. In an exemplary configuration, the lead 1310 has an outer diameter of approximately 1.375 inches and a thickness of 0.125 inch. The lead 1310 comprises a slot 1312 to receive a disposable sensor, or transmitter, 1320 such as a biosensor. The biosensor 1320 comprises an insulating member 1322 of approximately one (1) centimeter in diameter having a miniature rectangular conducting surface 1324 preferably constructed from silver and/or silver chloride. The conducting surface 1324 can be deposited using known deposition techniques such as ink-jet printing or screen-printing, the implementation of which is apparent to one of ordinary skill in the art. Moreover, the conducting surface 1324 can be patterned in various dimensions as to obtain desired sensitivity. Other combinations of metallic materials such as, but not limited to gold, platinum, and rhodium can be used to enhance the detection of selective ions making electrical connections with skin. A hydrogel layer 1326 is coated or printed onto the insulating member 1312 to cover the conducting surface 1324. The hydrogel layer 1326 provides a good electrical contact with ultrasound treated skin. A chemical agent may be further added to the hydrogel layer 1326 to condition and control the duration of low skin impedance for an extended period of time. For example, an osmotic agent or dermatological agent such as sodium chloride help keep skin properly hydrated during longer periods of ultrasound application.

The lead 400 further comprises an electronic circuit 1314, the implementation of which is apparent to one of ordinary skill in the art, to program a specific output impedance depending on the final impedance of the treated skin site measured by control box 1210. The lead 1310 preferably is attached to tissue interface receptacle 1010 and has a connector (not shown) to attach the biosensor 1320. Moreover, the lead 1310 further comprises a permanent or removable electrical cable (not shown) for coupling the biosensor 1320 to the inputs of various electrical signal analyzers.

In operation, skin preparation begins with attachment of tissue interface receptacle 1010 to a chosen tissue site 1020 such as the skin on the volar forearm of a human subject. The tissue interface receptacle 1010 is secured to the tissue 1020 the adhesive 1030. The reference lead 1220 is attached to another chosen skin site preferably on the biceps of a human subject. The ultrasonic applicator 1110 is placed on top of and subsequently inserted to mate concentrically with tissue interface receptacle 1010. The ultrasonic applicator 1110 is preferably held in place manually by a user during the skin preparation process. Upon actuation of the button 1170, an amount, e.g., five (5) cc, of the coupling media 1140 is introduced into the chamber 1150 by the control box 1210. The coupling media 1140 fills the passageway 1014 and the chamber 1150 to wet the chosen skin site and to immerse the tip of resonator 1120. In an embodiment of the invention, the coupling media 1140 is a fluid mixture comprising phosphate buffered saline (PBS) at a pH of 7, 1% by weight sodium laurel sulfate (SLS), and Tamsil 10 (Tamsil natural soft silica particles, grade 10). This fluid mixture provides rapid initiation and formation of cavitation upon the application of ultrasonic energy. Nonetheless, other suitable fluid mixtures, the identification of which is apparent to one of ordinary skill in the art, can be substituted for the coupling media 1140.

After the introduction of the coupling media 1140, the control box 1210 excites the resonator 1120 by activating the piezoelectric transducers 1130 with a sinusoidal signal of 55 kHz and of sufficient amplitude to deliver 10 Watts (W) of electrical energy to the resonator 1120 and subsequently to the coupling media 1140. Other frequencies of excitation, in the range of 20 kHz to 20 GHz, and energy amplitude 0.001 W to 10,000 W are also suitable to excite the coupling media. The ultrasound energy from the resonator 1120 promotes cavitation and other ultrasonic effects in the coupling media 1140 to disrupt the barrier properties of the chosen tissue 1020 site. Cavitation and other ultrasonic effects act on the stratum corneum portion of the skin site to disorder the lipid bilayer of the individual corneocytes as well as cleanse the site of dirt, grease, and dead cells.

During the delivery of ultrasonic energy to the coupling media 1140, the microcontroller 1212 of the control box 1210 applies a 10 Hz sinusoidal signal of 100 mV in amplitude using the signal generator 1213 to the body of the subject using the reference lead 1220 and the sensing lead 1230. Other operating parameters, such as square or sawtooth waveforms, frequencies in the range of 1 Hz to 100 GHz, and amplitudes in the range of nanovolts to kilovolts, preferably may be applied by microcontroller 1212. The microcontroller 1212 can also apply multiple sinusoidal signals to the body of the subject using the reference lead 1220 and the sensing lead 1230. The current, or any other electrical parameter as identified above, between the reference lead 1220 and the sensing lead 1230 is monitored by the microcontroller 1212 to determine the change in current between the leads 1220 and 1230. Optionally, the microcontroller 1212 can perform signal processing on the signal obtained from the sensing lead 1230 to reduce noise in the measurements.

The microcontroller 1212 performs a mathematical analysis to determine the characteristic profile of current changes between the reference leads 1220 and sensing 1230. Upon the determination of a characteristic profile such as a linear profile or a non-linear profile of current over time, the microcontroller 1212 performs calculations for specific mathematical parameters of the profiles. The mathematical parameters can be amplitude, frequency, rise time, initial values, and final values. These parameters can be obtained by applying various mathematical functions such as calculating the first derivative, calculating the second derivative, and calculating the nth-derivative. Other mathematical functions can be used to define the specific parameters of the characteristic profiles of current changes between the reference lead 1220 and the sensing lead 1230. Other signal-processing filters can be applied to the characteristic current changes to determine the characteristic parameters. The class of filters can include, but are not limited to Finite Impulse Response (FIR) and Infinite Impulse Response (IRR). The specific parameters measured are used by the microcontroller 1212 to determine a suitable time to terminate the application of ultrasonic energy to the coupling media 1140. Moreover, the microcontroller 1212 can also determine the initial and final skin impedance or conductance of the sonicated skin site. It can also utilize the information of the skin conductance or impedance to calculate the level of enhanced disruption of the protective barrier of the treated skin site. The microcontroller 1212 can change the amplitude, shape, frequency, and duration of excitation to the resonator 1120 in real-time during sonication.

A user can program the microcontroller 1212 using the user interface 1214 with various parameters as to determine the stopping point for skin preparation, as previously described. For example, a desired final skin conductance value or specific time duration of ultrasound application can be chosen. A user can also select a desired amplitude of the ultrasound energy applied to the coupling media 1140. Likewise, other parameters relating to subject information can be entered into the control box 1210. A system user also may query the final skin impedance at the treated site after treatment is complete.

Upon automatic termination of ultrasound energy by the microcontroller 1112, the coupling media 1140 is evacuated from the chamber 1150. The ultrasonic applicator 1110 can then be removed from the tissue interface receptacle 1010. Residual coupling media 1140 in receptacle 1010 is preferably removed using a gauze pad or the like. As previously mentioned, the lead 1310 is coupled to a disposable biosensor 1320 and comprises a variable impedance circuit (not shown), which can be programmed with a specific impedance to match or correlate to the impedance of the skin determined by the control box 1210 during sonication. Alternatively, leads of the desired impedance may be selected from among a number of leads having different impedances. The selection of matching or correlating impedances will be apparent to one of ordinary skill in the art in light of the present teachings. The lead 1310 is then inserted into the tissue interface receptacle 1010 and ready to be connected to the input of a diagnostic instrument such as an EEG, ECG, EKG, EMG, ERP, Surface EMG (SEMG), electrosomnographic device, electroretinograph, electrosurgical unit, Nasopharyngeal device, Holter instrument, Electrical Impedance Tomography (EIT) device, Multi-frequency Electrical Impedance Tomography (MFEIT) device, cardioscope, polygraphs, etc. and/or a treatment device such as Transcutaneous Electrical Nerve Stimulator (TENS), Electrical Muscle Stimulator (EMS), Neuromuscular Electrical Stimulation (NMES) device, pacemaker, defibrillator, etc.

In another embodiment of the invention, the electrode device 1300 can be integrated into the ultrasound applicator 1110 to form a single multi-purpose system.

Multiple sites on skin can be treated using additional tissue interface receptacles 1010. For example, multiple tissue interface receptacles 1010 can be placed individually throughout the body and head, arranged on a subject in a linear fashion as to create an array, or incorporated into a headgear for EEG applications requiring a standard number of skin sites. The control box 1210 can incorporate other hardware to control the application of various energy sources, such as coherent and non-coherent electromagnetic energy having a specific and non-specific wavelength and strength. The control box 1210 can also incorporate a laser capable of being focused on a specific cell, tissue area, or one or more organs for the purpose of ablating or creating an orifice or an array of holes. During such an ablation step, the reference lead 1220 and the sensing lead 1230 can be applied to the appropriate locations of cells, tissues, and organs in order to monitor the change in the level of impedance and to control the application of the laser energy. Moreover, the laser energy can be applied to cells, tissues, and organs or in their vicinities to create holes for enhancing electrical conductivity. If another source of energy is required such as a thermal source, then the appropriate source of energy element is replaced within the control box 1210. Because the function of the micro-controller 1212 in such a scenario is similar as that described for the application of ultrasound, the reference and sensing leads 1220 and 1230 can be employed to monitor the change in impedance of cells, tissues, and organs, in order to provide controlled ablation and subsequent preparation of a chosen site on a human or animal subject.

Figure 14:
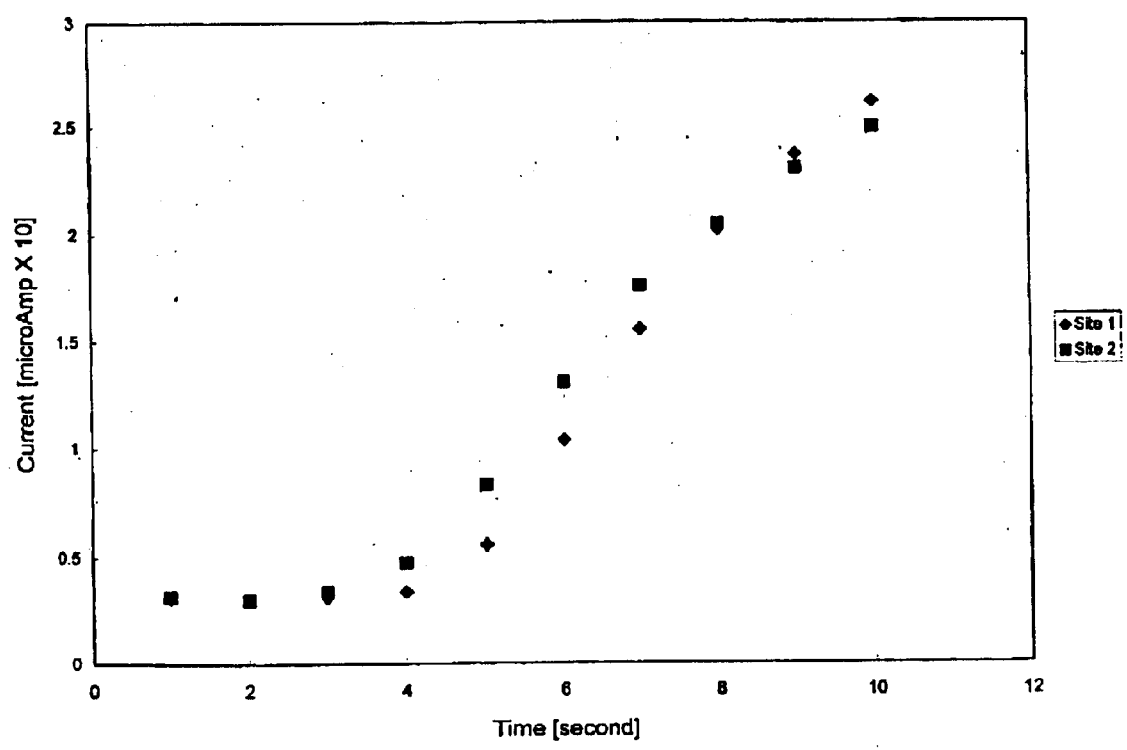
FIG. 14 illustrates an example characteristic conductance profile obtained from a human subject.

FIG. 14 illustrates a typical non-linear characteristic profile and provides an example of the convenient method of prepare skin for making electrical measurements described herein. Particularly, two skin sites on the volar forearm of a human subject were prepared using the method and system described above. The graph displays non-linear profiles of current between the reference lead 1220 and the sensing lead 1230 as a function of time. The current values at the beginning of the curve represent normal impedance values for untreated skin. The calculation of the skin impedance shows that the beginning skin impedance is 33,000 Ohms ($\Omega$). The calculation of the skin impedance at the final current value shows that the skin impedance of the treated site dropped to 4000 $\Omega$.

Two silver/silver chloride electrodes were introduced into separate tissue interface receptacle 1010 spaced approximately two inches apart on the forearm. A measurement was made by applying a 100 mV amplitude at 10 Hz sinusoidal signal to the treated sites with the two electrodes for 10 seconds. The current flowing through the skin was then measured. The impedance of the two treated sites was approximately at the same final current values on the graph. The short application time of 10 seconds shows that this skin preparation method is quick. The subject generally felt no discomfort during skin preparation for the two sites.

It is in the spirit of this invention to provide a method and system to treat cells, tissues, and organs so as to allow easy conduction of electrical signals in humans and animals. The method and system described provide a convenient and non-invasive means to prepare cells, tissues, and organs for electrical transmission and reception. It is anticipated that one of ordinary skill in the art can imagine and see the practical use of the mentioned method and systems in applications involving the transmission and reception of electrical signals through and into cells, tissues, and organs of humans and animals. The present invention is applicable to applications such as, but not limited to, the pretreatment of specific sites on a subject for electro-shock therapy; electrical stimulation and subsequent detection of magnetic signals; stimulation of acupuncture sites; reduction in the size of electrical pads and areas for electrical measurements; enhancing measurements of weak electrical signals for various medical diagnostic procedures such as myocardio infarction diagnosis and neurological disorder; enhancement of biomedical data acquisition; reducing motion artifacts for stress testing; improving signal distortion within electrical leads; and improving electrical communications and control of implanted devices located inside cells, tissues, and organs of humans and animals.

Although the invention has been particularly shown and described with reference to several preferred embodiments thereof, it will be understood by those skilled in the art that various changes in form and details may be made therein without departing from the spirit and scope of the invention as defined in the appended claims.

We claim:

1. A method for enhancing the transmission and reception of electrical signals through a tissue site comprising the steps of:

applying ultrasound to a tissue site to decrease an impedance of said tissue site, and affixing an electrode in proximity to said tissue site.

2. The method of claim 1, further comprising the step of measuring an electrical parameter of said tissue site.

3. The method of claim 2, wherein said electrical parameter corresponds to an impedance value of said tissue site.

4. The method of claim 3, further comprising the step of matching an impedance of said electrode to said impedance value of said tissue site.

5. The method of claim 3, further comprising the steps of:

analyzing said electrical parameter, and controlling said ultrasound application based on results of said analysis.

6. The method of claim 5, wherein said step of analyzing comprises the step of processing said measured electrical parameter to derive said impedance value of said tissue preparation site.

7. The method of claim 6, wherein said step of controlling comprises the step of discontinuing application of said ultrasound when said derived impedance value is substantially equal to or exceeds a predetermined value.

8. The method of claim 2, wherein said step of measuring an electrical parameter of said tissue site is performed during said step of applying ultrasound.

9. The method of claim 2, wherein said step of measuring an electrical parameter of said tissue site comprises the steps of:

affixing a first electrical lead to said tissue site, affixing a second electrical lead to a reference tissue site, and applying an electrical potential difference between said first and second electrical leads.

10. The method of claim 9, wherein said electrical potential difference is an alternating current potential.

11. The method of claim 9, wherein said electrical parameter is a current amount flowing between said tissue site and said reference tissue site.

12. The method of claim 2, wherein said electrical parameter is selected from the group consisting of:

current value, current value change during a specified time period, instantaneous rate of current value change, impedance value at said tissue site, impedance value change at said tissue site during a specified time period, difference of impedance values between said tissue site and said reference tissue site.

13. The method of claim 1, wherein said step of applying said ultrasound to said tissue site comprises the steps of:

affixing an interface receptacle to said application tissue site, and holding an ultrasound source against said interface receptacle.

14. The method of claim 13, wherein said electrode is affixed to said interface receptacle upon termination of said step of applying said ultrasound to said tissue site.

15. The method of claim 1, further comprising the step of acquiring a bioelectrical signal at said tissue preparation site via said electrode.

16. A method for measuring bioelectrical signals comprising the steps of:

applying ultrasound to a tissue site to decrease an impedance of said tissue site, placing a biosensor electrode in proximity to said tissue site, and measuring a bioelectric signal generated at said biosensor electrode.

17. The method of claim 16, further comprising the step of measuring an impedance value of said tissue site.

18. The method of claim 17, further comprising the step of matching an impedance of said biosensor electrode to said impedance value of said tissue site.

19. The method of claim 17, wherein said step of measuring said impedance value of said tissue site comprises the steps of:

affixing a first electrical lead to said tissue site, affixing a second electrical lead to a reference tissue site, and applying an electrical potential difference between said first and second electrical leads.

20. The method of claim 16, wherein said step of applying said ultrasound to said tissue site comprises the steps of:

affixing an interface receptacle to said application tissue site, and holding an ultrasound source against said interface receptacle.

21. The method of claim 20, wherein said biosensor electrode is affixed to said interface receptacle upon termination of said step of applying said ultrasound to said tissue site.

22. The method of claim 16, further comprising the step of acquiring a bioelectrical signal at said tissue preparation site via said biosensor electrode.

\* \* \* \* \*